(12) United States Patent
Akutsu et al.

(10) Patent No.: US 9,108,832 B2
(45) Date of Patent: Aug. 18, 2015

(54) COVER OPENER AND AUTOMATIC ANALYZING DEVICE USING SAME

(75) Inventors: Masanori Akutsu, Hitachinaka (JP); Takeshi Shibuya, Hitachinaka (JP)

(73) Assignee: HITACHI HIGH TECHNOLOGIES CORPORATION, Tokyo (JP)

( * ) Notice: Subject to any disclaimer, the term of this patent is extended or adjusted under 35 U.S.C. 154(b) by 46 days.

(21) Appl. No.: 13/503,952

(22) PCT Filed: Nov. 1, 2010

(86) PCT No.: PCT/JP2010/069449
§ 371 (c)(1),
(2), (4) Date: Apr. 25, 2012

(87) PCT Pub. No.: WO2011/055712
PCT Pub. Date: May 12, 2011

(65) Prior Publication Data
US 2012/0213668 A1     Aug. 23, 2012

(30) Foreign Application Priority Data
Nov. 4, 2009   (JP) ................. 2009-253150

(51) Int. Cl.
| | |
|---|---|
| *B65B 43/40* | (2006.01) |
| *B67B 7/18* | (2006.01) |
| *B01L 3/00* | (2006.01) |
| *G01N 35/04* | (2006.01) |

(52) U.S. Cl.
CPC ............. *B67B 7/182* (2013.01); *B01L 3/50825* (2013.01); *G01N 35/04* (2013.01); *B01L 2200/025* (2013.01); *B01L 2300/042* (2013.01); *B01L 2300/046* (2013.01); *G01N 2035/0405* (2013.01)

(58) Field of Classification Search
CPC ................. G01N 2035/0405; B01L 3/50825; B01L 2300/042; B01L 2300/046
See application file for complete search history.

(56) References Cited

U.S. PATENT DOCUMENTS 3,683,598 A    8/1972   Van Zijp
(Continued)

FOREIGN PATENT DOCUMENTS

| DE | 2146533 A1 | 5/1973 |
|---|---|---|
| EP | 1914556 A2 | 4/2008 |
| EP | 2031407 A1 | 3/2009 |
| JP | 07-018265 A | 1/1995 |
| JP | 07-029464 A | 1/1995 |

(Continued)

OTHER PUBLICATIONS

Extended European Search Report received in corresponding European Application No. 10828272.4 dated May 19, 2015.

*Primary Examiner* — P. Kathryn Wright
(74) *Attorney, Agent, or Firm* — Mattingly & Malur, PC

(57) ABSTRACT

A cover opener for opening a cover 1*a* that is rotationally removed from and fixed to a reagent container 1 includes: a rotational drive unit 12 and a cover retainer 17 to retain the cover 1*a* by becoming engaged with a concave portion 1*b* provided on an upper portion of the cover 1*a*. A carrier 16 is driven to rotate as the rotational drive unit rotates, as well as to move in a direction of a rotational axis with respect to the rotational drive unit. Springs 19 and 20, one of which is provided between the rotational drive unit and the cover retainer, and the other between the rotational drive unit and the carrier, bias the rotational drive unit and the cover retainer or the carrier in relative fashion to move away from each other. This enables the cover of the reagent container to be reliably opened.

6 Claims, 5 Drawing Sheets

(56) References Cited

U.S. PATENT DOCUMENTS

| | | |
|---|---|---|
| 3,987,535 A | 10/1976 | Brown |
| 4,678,752 A * | 7/1987 | Thorne et al. ............ 435/287.3 |
| 2005/0013742 A1 | 1/2005 | Shaw |
| 2009/0056285 A1 | 3/2009 | Kramer et al. |

FOREIGN PATENT DOCUMENTS

| | | |
|---|---|---|
| JP | 200-146985 A | 5/2000 |
| JP | 2004-294428 A | 10/2004 |
| JP | 2006-27704 A | 2/2006 |
| JP | 2009-058509 A | 3/2009 |

* cited by examiner

COVER OPENER AND AUTOMATIC ANALYZING DEVICE USING SAME

TECHNICAL FIELD

The present invention relates to a cover opener for containers that each accommodate such a biological sample as of serum or urine, or a chemical such as a reagent, and to an automatic analyzing device using the same.

BACKGROUND ART

Automatic analyzing devices, intended to analyze samples (e.g., biological samples of serum, urine, or the like, or liquid mixtures thereof with reagents) by assaying physical properties of these samples or mixtures, include constituent elements relating to various steps such as container cover opening, chemicals dispensing, stirring, and analyzing.

As described in Patent Documents 1 to 3 below, conventional techniques relating to a cover opener which opens a cover of a container in the respective cover-opening steps of those automatic analyzing devices are each targeted for a sample container accommodating a sample to be assayed (the cover-opening step in each such device is hereinafter referred to as the cover opening process).

The cover opener described in Patent Document 1 (JP-UM-1995-18265-A) includes a cover opening member provided with a gripping portion having a gripping arm to grip an outer circumferential surface of a head portion of a rubber cover mounted over a blood collection tube which is a sample container. The cover opening member also has a plate that is engaged with the cover opening member by a pin provided above the gripping portion of the cover opening member. Upon moving the plate in a horizontal direction by activating horizontal moving means, the cover opener causes the cover opening member to incline with the gripping portion fixed to the rubber cover, as a center, thus conducting the cover opening process by removing the cover from the blood collection tube (sample container).

The cover opener described in Patent Document 2 (JP-UM-1995-29464-A) includes a cover opening member that moves forward from an obliquely downward direction, in an obliquely upward direction, towards a rubber cover of a sample container, or vice versa. The cover opening member presses a front end of its spring plate against the rubber cover in a forward moving stroke of the opening member, then pushes the cover further obliquely upward, thereby conducting the cover opening process by removing the rubber cover from the sample container.

The cover opener described in Patent Document 3 (JP-2000-146985-A) includes a rubber-cover gripping chuck that grips a rubber cover of a sample container, the rubber-cover gripping chuck, after gripping the rubber cover, oscillatingly moving upward to conduct the cover opening process by drawing the rubber cover from a vacuum tube.

In addition, other conventional techniques relating to a cover opener which conducts the cover opening process upon a reagent container accommodating a reagent are described in Patent Documents 4 and 5.

The cover openers described in Patent Document 4 (JP-2004-294428-A) and Patent Document 5 (JP-2009-58509-A) are those which open a cover that is rotationally removed from and fixed to the reagent container, the cover having a concave portion on its upper surface in addition to a tooth-like structure on an outer circumferential portion of the upper surface. These cover openers each include a snap-in element provided at a lower end of a centering unit, for engagement with the concave portion in the cover, and a carrier having a capture element for securing to the tooth-like structure of the cover. The snap-in element holds the cover and the carrier rotates the cover, whereby the opener conducts the cover opening process.

PRIOR ART LITERATURE

Patent Documents

Patent Document 1: JP-UM-1995-18265-A
Patent Document 2: JP-UM-1995-29464-A
Patent Document 3: JP-2000-146985-A
Patent Document 4: JP-2004-294428-A
Patent Document 5: JP-2009-58509-A

SUMMARY OF THE INVENTION

Problems to be Solved by the Invention

In the conventional technique of Patent Document 4, however, although the carrier is configured to be movable vertically in relative fashion with respect to the centering unit, the snap-in element is fixed in relative form with respect to the centering unit. Merely adjusting a vertical position of the centering unit, therefore, may not suffice for accommodating geometrical or dimensional nonuniformity of the concave portion in the cover of the reagent container, and if the nonuniformity is unaccommodable, the cover opening process could lack reliability since improper hold of the cover is likely.

Furthermore, since the cover opener described in Patent Document 5 (JP-2009-58509-A) is configured so that the carrier and the centering unit with the snap-in element are fixed in relative form, this configuration is susceptible to not only the geometrical or dimensional nonuniformity of the concave portion in the cover of the reagent container, but also that of the entire cover including the tooth-like structure. As in the conventional technique of Patent Document 4, therefore, if the nonuniformity is unaccommodable, the cover opening process could lack reliability since improper hold of the cover is likely.

The present invention has been made with the above held in view, and an object of the invention is to provide a cover opener that reliably opens a cover of a reagent container, and an automatic analyzing device using the opener.

Means for Solving the Problems

In order to attain the above object, a cover opener of the present invention, designed to open a cover that is rotationally removed from and fixed to a reagent container, includes: a rotational drive unit driven by rotational driving means to rotate about a rotational axis of the cover; a cover retainer provided at an opposed position with respect to a concave portion on an upper portion of the cover so as to move in a direction of the rotational axis with respect to the rotational drive unit, the cover retainer becoming engaged with the concave portion and thereby retaining the cover; a carrier provided at an opposed position with respect to the cover and including a plurality of protrusions formed for engagement with a plurality of grooves spaced from each other on an upper outer circumference of the cover, the carrier being driven to rotate as the rotational drive unit rotates, as well as to move in the direction of the rotational axis with respect to the rotational drive unit; means for biasing the cover retainer in relative fashion with respect to the rotational drive unit to move away from each other; and means for biasing the carrier in relative fashion with respect to the rotational drive unit to move away from each other.

Effects of the Invention

In accordance with the present invention, the cover of the reagent container can be reliably opened.

MODE FOR CARRYING OUT THE INVENTION

Hereunder, an embodiment of the present invention will be described referring to the accompanying drawings.

Figure 8:
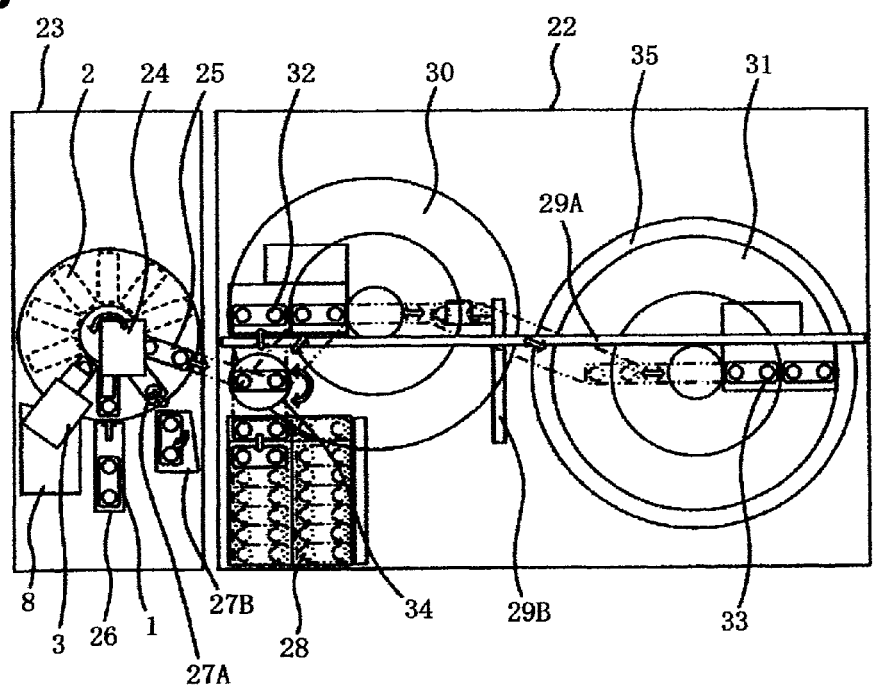
FIG. 8 is a schematic view showing an overall configuration of an automatic analyzing device according to the embodiment of the present invention.

FIG. 8 is a schematic view showing an overall configuration of an automatic analyzing device according to the embodiment of the present invention.

Referring to FIG. 8, the automatic analyzing device according to the present embodiment includes an analyzing unit 22 and a reagent replenishing unit 23. While the analyzing unit 22 and the reagent replenishing unit 23 are provided as separate elements in the present embodiment, the two elements can instead be formed as an integrated unit. In addition, if both elements are provided separately as described above, only the analyzing unit 22 can be used independently.

The automatic analyzing device according to the present embodiment undertakes analysis under management of a control computer (not shown) that controls the entire analyzing device. The analyzing unit 22 and the reagent replenishing unit 23, each equipped with a specific control circuit and control device managed by the control computer, are managed and controlled under the control computer by the respective control circuits and control devices. The control computer also has a function of supply executable/or not determination means. An operator performs analyses while, for example, watching an operating screen display for the control computer, and/or operating control switches or buttons.

The analyzing unit 22 and the reagent replenishing unit 23 each includes a power supply, a controller, and drives that drivingly control various constituent elements, various mechanisms, or various forms of means, of the unit. A reagent information reading mechanism 24, the supply executable/or not determination means, reagent container elimination means, analytical measurement with the analyzing unit 22, and internal operation of the analyzing unit 22, such as reagent container transport and discarding, are also controlled and operated/conducted.

In addition, the above control circuits and control devices provide functional/operational control relating to loading reagent containers into the reagent replenishing unit 23, transporting each reagent container from the reagent replenishing unit 23 to the analyzing unit 22, and eliminating, from a replenishment reagent container storage section, reagent containers unusable for analysis. The control circuits and the control devices further conduct rotational driving control of the replenishment reagent container storage section and dispensing-use reagent container storage sections.

The analyzing unit 22 includes the dispensing-use reagent container storage sections (A) 30 and (B) 31 for storage of dispensing-use reagent containers. The dispensing-use reagent container storage section (A) 30 is positioned near the reagent replenishing unit 23, and the dispensing-use reagent container storage section (B) 31 is positioned away from the reagent replenishing unit 23. An analyzing mechanism 35 that includes reaction vessels and measuring instruments is disposed around the dispensing-use reagent container storage section (B) 31.

The dispensing-use reagent container storage section (A) 30, the dispensing-use reagent container storage section (B) 31, and the analyzing mechanism 35 are of a rotatable disk type. In each of the dispensing-use reagent container storage section (A) 30 and the dispensing-use reagent container storage section (B) 31, two disks are arranged on inner and outer surfaces of the storage section so as to form a double disk structure.

The dispensing-use reagent container storage section (A) 30 has a reagent container loading port (A) 32 at its upper side, and the dispensing-use reagent container storage section (B) 31 has a reagent container loading port (B) 33 at its upper side. Dispensing-use reagent containers are stored from the loading ports into the disks.

The analyzing unit 22 further includes reagent transfer means to transport reagent containers. The reagent transfer means includes a first reagent container transfer mechanism 25, a second reagent container transfer mechanism 29, and a reagent container transfer relay section, all of the three elements being equipped at a side of the reagent replenishing unit 23.

The following describes the second reagent container transfer mechanism 29 and the reagent container transfer relay section.

The second reagent container transfer mechanism 29 includes, for example, transport guide rails 29A and 28B that constitute a transport mechanism. The analyzing unit 22 has a reagent container rotating mechanism 34 adjacent to the reagent container loading port (A) 32 of the dispensing-use reagent container storage section (A) 30. The reagent container rotating mechanism 34 operates as the reagent container transfer relay section. The analyzing unit 22 further has a reagent container discarding storage section 28 at an opposite side of the reagent container loading port (A) 32, across the reagent container rotating mechanism 34. The reagent container rotating mechanism 34, used for changing a direction of a reagent container which has been transferred from the reagent replenishing unit 23 to the reagent container rotating mechanism 34, thereby makes it easy for the second reagent container transfer mechanism 29 at a side of the analyzing unit 22 to hold the reagent container.

The second reagent container transfer mechanism 29 at the side of the analyzing unit 22 is constructed so that while being guided by the transport guide rail 29B, the transport guide rail 29A moves between the reagent container loading port (A) 32 and the reagent container discarding storage section 28 via the reagent container rotating mechanism 34. In addition, the transport guide rail 29A is of such length as it ranges from a region of the reagent container loading port (A) 32 of the dispensing-use reagent container storage section (A) 30 to a region of the reagent container loading port (B) 33 of the dispensing-use reagent container storage section (B) 31.

The second reagent container transfer mechanism 29 at the side of the analyzing unit 22 carries the above-mentioned reagent container transferred from the reagent replenishing unit 23 to the reagent container rotating mechanism 34, to the reagent container loading port (A) 32 of the dispensing-use reagent container storage section (A) 30 or the reagent container loading port (B) 33 of the dispensing-use reagent container storage section (B) 31, and then stores the container into the appropriate disk. The second reagent container transfer mechanism 29 also carries in a used reagent container from the reagent container storage section (A) 30 or the reagent container storage section (B) 31, and transports the used reagent container to the reagent container discarding storage section 28.

The reagent replenishing unit 23 includes a reagent transport disk 2. The reagent transport disk 2 is for storing replenishment reagent containers 1 before the containers are supplied as dispensing-use reagent containers to the dispensing-use reagent container storage section (A) 30 and the dispensing-use reagent container storage section (B) 31. The reagent transport disk 2 can be rotated.

The reagent replenishing unit 23 includes dispensing-use reagent container loading means 26. The dispensing-use reagent container loading means 26 has a loading port (not shown) from which a dispensing-use reagent container 1 is to be loaded. The dispensing-use reagent container 1, after being loaded from the loading port, is further loaded into the reagent transport disk 2 by the dispensing-use reagent container loading means 26.

The reagent replenishing unit 23 includes the first reagent container transfer mechanism 25, one element of the reagent transfer means described above. The dispensing-use reagent container 1 in the reagent transport disk 2 is transported by the first reagent container transfer mechanism 25 to the reagent container rotating mechanism 34 of the reagent transfer means equipped in the analyzing unit 22. The reagent container rotating mechanism 34 slightly turns to change a direction of the dispensing-use reagent container 1 which has been carried to the reagent container rotating mechanism 34. This change in direction makes it easy for the reagent transfer means to hold the replenishment reagent container and transfer this container to the dispensing-use reagent container storage section (A) 30 or the dispensing-use reagent container storage section (B) 31.

The reagent replenishing unit 23 further has reagent container elimination means 27A that eliminates unusable replenishment reagent containers from the reagent transport disk 2, and a receptacle 27B for accommodating eliminated reagent containers.

Those replenishment reagent containers in the reagent transport disk 2 that are unusable for analysis are unsuitable for supply to the dispensing-use reagent container storage section (A) 30 or the dispensing-use reagent container storage section (B) 31, so these unusable replenishment reagent containers are eliminated by the reagent container elimination means 27A and placed on the receptacle 27B.

The reagent replenishing unit 23 further has a reagent information reading mechanism 24 that reads information from each replenishment reagent container in the reagent transfer disk 2. The replenishment reagent container information that the information reading mechanism 24 has read is supplied to the supply executable/or not determination means, this means then determining whether the reagent container is to be supplied to the dispensing-use reagent container storage section (A) 30 or the dispensing-use reagent container storage section (B) 31.

The reagent container, if determined by the supply executable/or not determination means to be supplied to the dispensing-use reagent container storage section (A) 30 or the dispensing-use reagent container storage section (B) 31, will be transferred thereto by the reagent transfer means. If determined not to be supplied, however, the reagent container will be unloaded from the reagent transport disk 2 by the reagent container elimination means 27A.

The reagent replenishing unit 23 further has a cover opener 3 that removes covers 1*a* of replenishment reagent containers, and a box 8 for discarding removed covers 1*a*. After a replenishment reagent container has been placed on the reagent transport disk 2, the cover opener 3 removes the cover 1*a* of the container and then the reagent transfer means transfers the container to the dispensing-use reagent container storage section (A) 30 or the dispensing-use reagent container storage section (B) 31.

Figure 1:
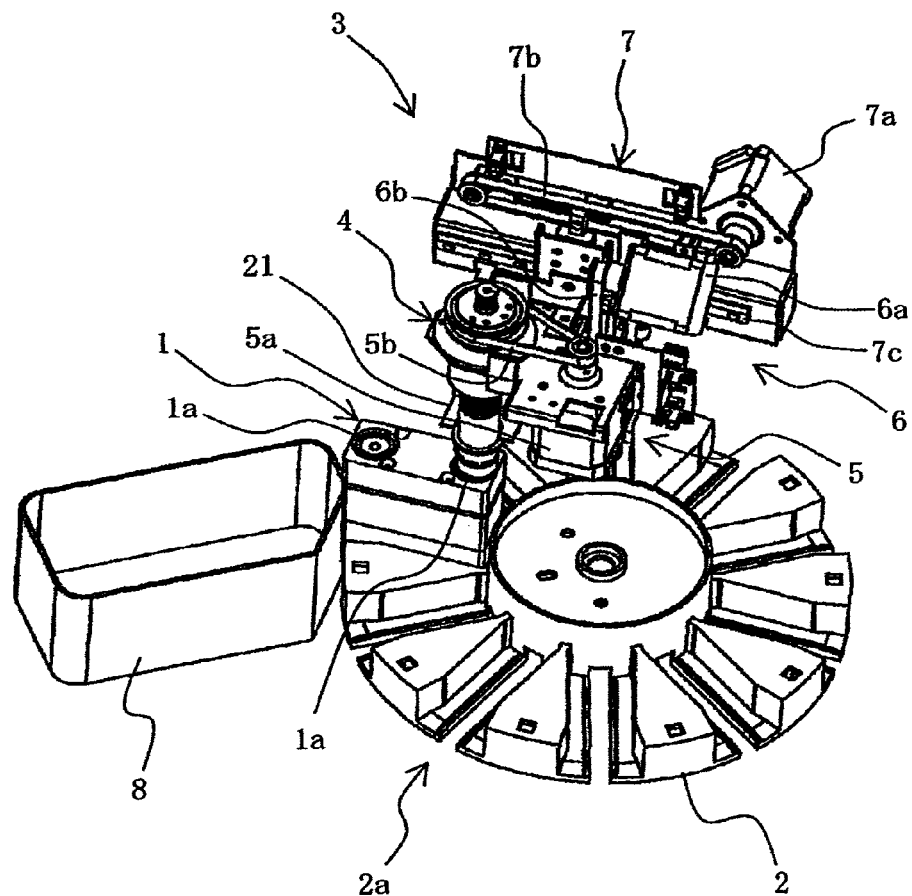
FIG. 1 is a schematic view showing a configuration of a reagent replenishing unit equipped with a cover opener according to an embodiment of the present invention.

FIG. 1 is a schematic view showing a configuration of the reagent replenishing unit 23.

Referring to FIG. 1, the reagent replenishing unit 23 substantially includes the reagent transport disk 2 that retains and transports a reagent container 1 accommodating a reagent, and the cover opener 3 that conducts a cover opening process upon the reagent container 1 transported by the reagent transport disk 2.

The reagent container 1 has at least one opening for accommodating and removing the reagent, and each opening in the container is blocked with the cover 1*a* for suppressing evaporation, and the like, of the reagent contained inside.

Figure 2:
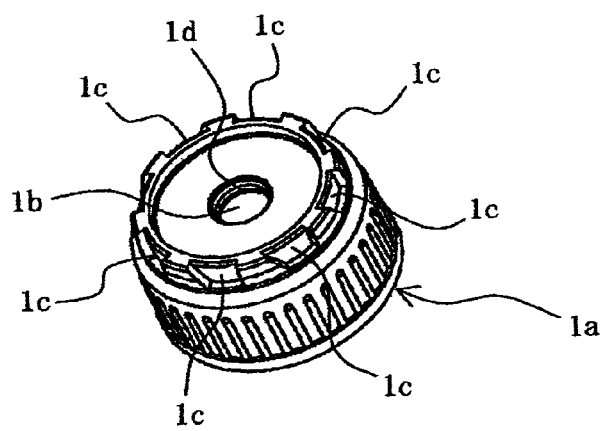
FIG. 2 is an enlarged view showing a cover of a reagent container.

FIG. 2 is an enlarged view showing the cover 1*a* of the reagent container 1.

Referring to FIG. 2, the cover 1*a* has a cartridge-like or cylindrical shape closed at one end, as shown, the cover 1*a* including a concave portion 1*b* provided at the closed end (hereinafter, referred to as the upper surface), and a plurality of (say, eight) grooves 1*c* spaced from each other around the concave portion 1*b* on an upper circumferential section of the cover 1*a*.

An annular convex portion 1*d* that engages with an annular groove 17*a* provided on a cover retainer 17 (described later) is formed on an inner circumferential section of the concave portion 1*b* in the cover 1*a*. See FIGS. 6 and 7 for the annular groove 17*a*. The engagement between the annular groove 17*a* and the annular convex portion 1*d* makes the cover retainer 17 retain the cover 1*a*.

The cover 1*a* having a screw shape (not shown) on its inner side is also constructed to mate with a screw-shaped pitch that is provided in each opening of the reagent container 1. Circumferential rotation of the cover 1*a* causes the cover to be removed from and fixed to the openings in the reagent container 1. The process of removing the cover 1*a* from the opening in the reagent container 1 is hereinafter referred to as the cover opening process.

FIG. 1 is referred.

The reagent transport disk 2 is means for transporting reagent containers 1 to an executing position for the cover opening process, and has a plurality of retainers 2a to retain the reagent containers 1. In FIG. 1, on behalf of the retainers 2a, one of them is shown with the reference number, and for the remaining retainers 2a, the reference number is omitted for simplicity of the drawing. FIG. 1 shows an example in which a reagent container 1 is retained by one of the retainers 2a. The reagent container 1 is transported upon the reagent transport disk 2 being rotationally driven by a rotational driving device not shown.

The cover opener 3 includes a cover opening mechanism 4 (described later), a rotational driving mechanism 5 for rotationally driving a pulley 12a (see FIG. 3) of the cover opening mechanism 4, a vertical moving mechanism 6 for driving integrally the cover opening mechanism 4 and the rotational driving mechanism 5 in vertical directions, a horizontal moving mechanism 7 for driving integrally the cover opening mechanism 4, the rotational driving mechanism 5, and the vertical moving mechanism 6 in horizontal directions. The cover opener 3 also includes the above-mentioned discarding box 8 for discarding the cover 1a removed from the openings of the reagent container 1 during the cover opening process of the cover opening mechanism 4.

The rotational driving mechanism 5 includes a rotational driving motor 5a and a belt that transmits driving force of the motor 5a to the pulley 12a (described later) of the cover opening mechanism 4.

The vertical moving mechanism 6 includes a vertical driving motor 6a, a belt 6b that transmits driving force of the motor 6a, and a guide rail (not shown) that extends in a vertical direction. The cover opening mechanism 4 and the rotational driving mechanism 5 are connected to the belt 6b, and are moved integrally in vertical directions along the guide rail by the driving force of the motor 6a.

The horizontal moving mechanism 7 includes a horizontal driving motor 7a, a belt 7b that transmits driving force of the motor 7a, and a guide rail 7c that extends in a horizontal direction. The vertical moving mechanism 6 is connected to the belt 7b, and the cover opening mechanism 4, the rotational driving mechanism 5, and the vertical moving mechanism 6 are moved integrally in the vertical directions along the guide rail 7c by the driving force of the motor 7a.

Figure 3:
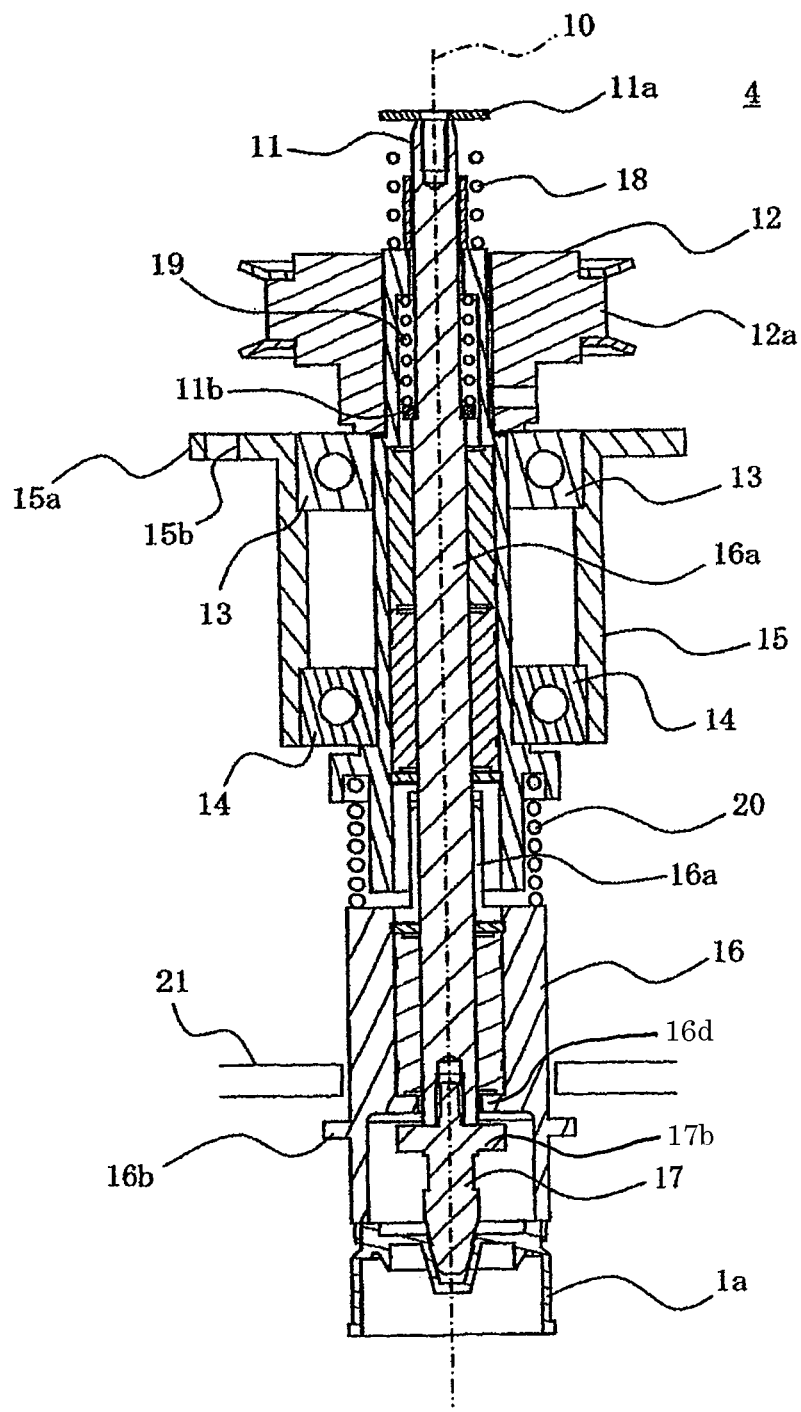
FIG. 3 is a longitudinal cutaway showing a cover opening mechanism of the cover opener in extractive form, the cutaway representing the way the cover opening mechanism retains the cover.
Figure 4:
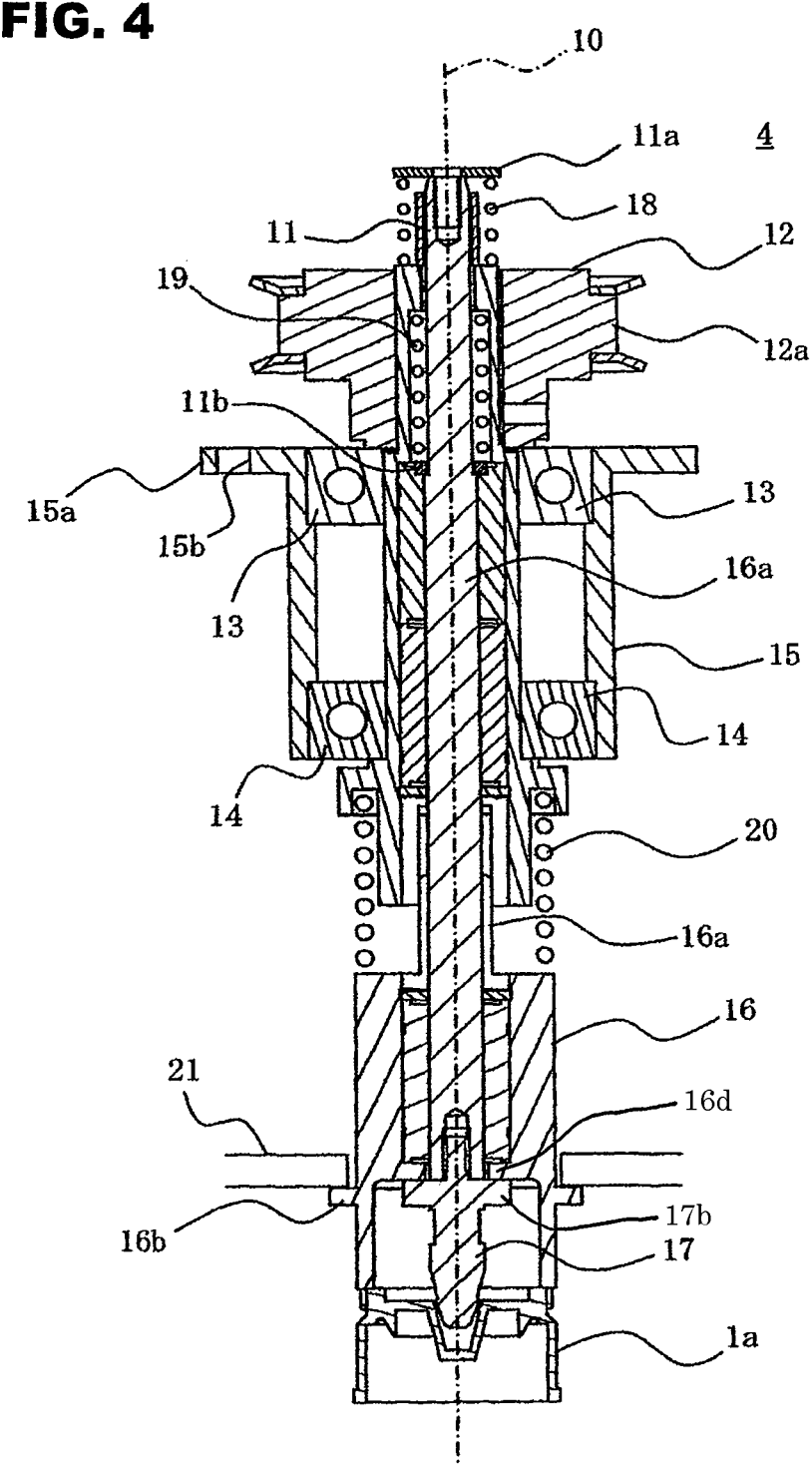
FIG. 4 is another longitudinal cutaway showing the cover opening mechanism of the cover opener in extractive form, the cutaway representing the way the cover opening mechanism discards the cover.
Figure 5:
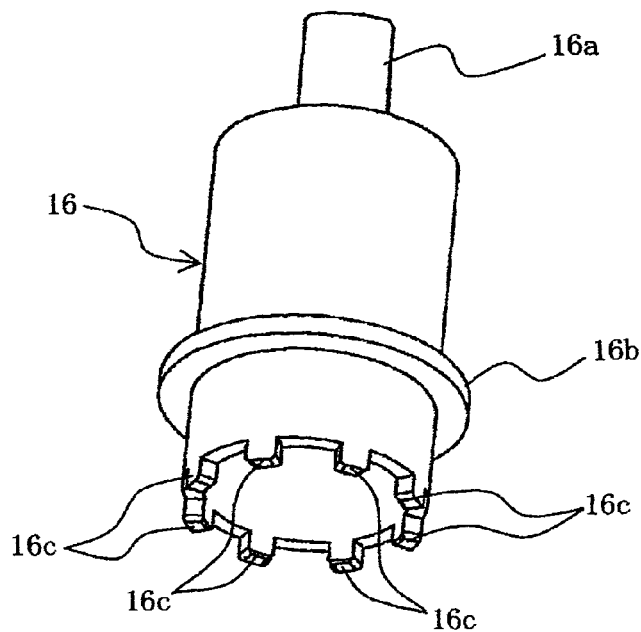
FIG. 5 is a diagram showing a carrier of the cover opening mechanism in extractive form.

FIGS. 3 and 4 are longitudinal cutaway diagrams showing in extractive form the cover opening mechanism 4 shown in FIG. 1, FIG. 3 representing the way the cover opening mechanism 4 retains the cover 1a, and FIG. 4 representing the way the cover opening mechanism 4 releases the cover 1a from it for discarding. FIG. 5 is a diagram showing in extractive form the carrier 16 of the cover opening mechanism 4 shown in FIGS. 3 and 4.

Referring to FIGS. 3 and 4, the cover opening mechanism 4 substantially includes: a shaft 11 provided along a central axis 10 of the cover opening mechanism 4; a rotational drive unit 12 provided concentrically on an outer circumference of the shaft 11; a base 15 provided concentrically on an outer circumference of the rotational drive unit 12 via bearings 13 and 14; the carrier 16 provided concentrically on the outer circumference of the shaft 11, below the base 15; the cover retainer 17 provided at a lower end of the shaft 11; a third spring 18 placed through the shaft 11 centrally between a stopper 11a provided at an upper end of the shaft 11 in order to prevent the shaft 11 from shifting downward and falling, and an upper portion of the rotational drive unit 12, the third spring 18 alleviating a shock that may occur between the stopper 11a and the rotational drive unit 12; a first spring 19 placed across the shaft 11, in a space present partly between the shaft 11 and the rotational drive unit 12, the first spring 19 biasing the shaft 11 downward with respect to the rotational drive unit 12 by biasing the rotational drive unit 12 downward via a spring bearing 11b fixed to the shaft 11; a second spring 20 placed through the shaft 11 centrally between a lower portion of the rotational drive unit 12 and an upper portion of the carrier 16, for biasing the carrier 16 downward with respect to the rotational drive unit 12; and a discarding stopper 21 that abuts the convex portion 16b of the carrier 16 during the discarding of the cover 1a and thereby limits upward movement of the carrier 16. In addition, as shown in FIGS. 3 and 4, the carrier 16 also has a protrusion (projection) 16d extending inwardly from the inner surface of the carrier.

The rotational drive unit 12 and the carrier 16 are provided to be slidable in a vertical direction (axially along the central axis 10) relative to the shaft 11, and to be rotatable about the shaft 11. The rotational drive unit 12 is further provided to be rotatable about an axis of the base 15 and so as not to move vertically relative to the base 15.

The carrier 16 has an upper end 16a disposed coaxially with respect to the shaft 11 at a lower end of the rotational drive unit 12 and so as to be slidable in the vertical direction (axially along the central axis 10) relative to the rotational drive unit 12, via a spline structure not shown, the upper end 16a also being provided so as not to rotate in relative form in the axial direction. In other words, when the carrier 16 rotates about the shaft 11, the carrier is driven to rotate integrally with the rotation of the rotational drive unit 12.

The base 15 has a flange 15a on its outer circumference, the flange 15a being fixed to the rotational driving mechanism 5 through a fixing hole 15b provided in the flange.

The rotational drive unit 12 has the pulley 12a connected to the motor 5a of the rotational driving mechanism 5 via the belt 5a, and is rotationally driven by the driving force that the motor 5a of the rotational driving mechanism 5 generates.

Referring to FIG. 5, the carrier 16 has a cylindrical shape with an open lower end, at the end of which are provided a plurality of (say, eight) protrusions 16c that engage with the plurality of (say, eight) grooves 1c of the cover 1a. After the protrusions 16c on the carrier 16 and the grooves 1c of the cover 1a have become engaged, the carrier is driven to rotate axially, whereby the cover 1a is rotationally driven to be opened.

The first spring 19 here is the means provided between the rotational drive unit 12 and the cover retainer 17, for biasing the cover retainer 17 in the direction of its axial rotation, towards the cover, as well as biasing the rotational drive unit 12 in a direction opposite to that direction, the first spring 19 constituting a first means to bias the rotational drive unit 12 and the cover retainer 17 in relative fashion to move away from each other. The second spring 20 is the means provided between the rotational drive unit 12 and the carrier 16, for biasing the carrier 16 in the direction of its axial rotation, towards the cover, as well as biasing the rotational drive unit 12 in a direction opposite to that direction, the second spring 20 constituting a second means to bias the rotational drive unit 12 and the carrier 16 in relative fashion to move away from each other.

The cover 1a, the carrier 16, and the cover retainer 17 are further detailed below referring to FIGS. 6 and 7.

Figure 6:
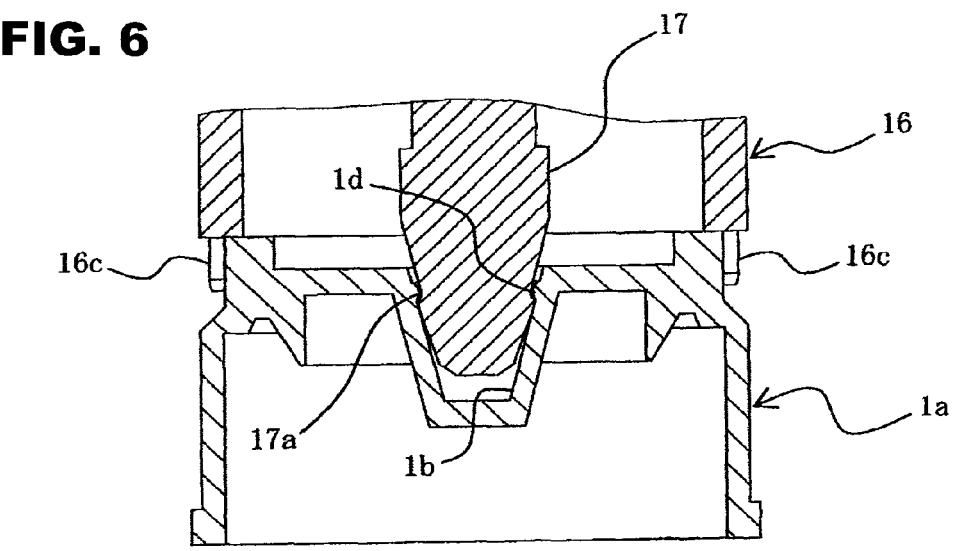
FIG. 6 is a sectional view showing a cover retainer and its periphery in enlarged form, the view representing the way the cover retainer retains the cover.
Figure 7:
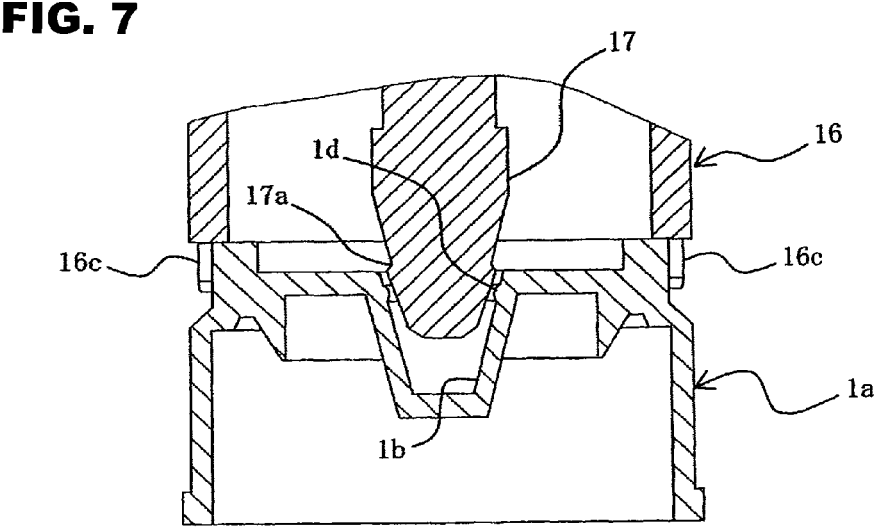
FIG. 7 is another sectional view showing the cover retainer and the periphery in enlarged form, this sectional view representing the way the cover retainer releases the cover.

FIGS. 6 and 7 are sectional views showing the cover retainer 17 and its periphery in enlarged form, FIG. 6 representing the way the cover retainer 17 retains the cover 1a, and FIG. 7 representing a state of the cover retainer 17 existing immediately after being released the cover 1a.

As shown in FIG. 6, after insertion of the cover retainer 17 into the concave portion 1b of the cover 1a, the annular convex portion 1d of the cover 1a and the annular groove 17a of the cover retainer 17 become engaged, thus making the cover retainer 17 retain the cover 1a. Additionally, as shown in FIG. 7, after relative upward driving of the cover retainer 17 with respect to the carrier 16, upon the upward driving force exceeding the force occurring during the above engagement, the cover 1a is released from the cover retainer 17. The cover retainer 17 is provided to be replaceable with respect to the shaft 11, and can be replaced with an appropriate cover retainer according to particular specifications (shape, dimensions, depth, etc.) of the cover 1a or of the concave portion 1b.

The cover retainer 17 works together with the stopper 11a at the upper end of the shaft 11, to restrict downward shifts in the positions of the rotational drive unit 12 and carrier 16 from the shaft 11. Therefore, an unexpected downward movement of the rotational drive unit 12 from the shaft 11 is suppressed by the stopper 11a, and an unexpected downward movement of the carrier 16 from the shaft 11 is suppressed by the cover retainer 17 serving as a stopper, provided at the lower end of the shaft 11. Furthermore, the shaft 11 has its length preset to a value that prevents the upper end 16a of the carrier 16 from coming off from the lower end of the rotational drive unit 12 even if the rotational drive unit 12 shifts to the upper end of the shaft 11 (i.e., one end of the stopper 11a) and/or the carrier 16 shifts to the lower end of the shaft 11 (i.e., one end of the cover retainer 17).

Operation of the cover opener in the present embodiment having the above configuration is described below.

First, a reagent container 1 is placed on the retainer 2a of the reagent transport disk 2, and the reagent transport disk 2 is rotationally driven to move the reagent container 1 to a cover opening position provided below the cover opener 3.

Next, the horizontal moving mechanism 7 moves the cover opening mechanism 4 to a position above the cover 1a of the reagent container 1 to be subjected to cover opening, and then the vertical moving mechanism 6 moves the cover opening mechanism 4 downward towards the cover 1a.

As shown in FIGS. 3 and 4, the carrier has a protrusion (projection) 17b extending outwardly, from the outer surface of the cover retainer, along the circumferential direction. After the downward movement of the cover opening mechanism 4, the cover retainer 17 is inserted into the concave portion 1b of the cover 1a and positioned there. The protrusions 16c on the carrier 16 then fit into the grooves 1c of the cover 1a. At this time, the second spring 20 contracts to absorb any excess of the downward travel of the cover opening mechanism 4, that is, a distance through which the cover opening mechanism 4 may move downward after the protrusions 16c have fitted into the grooves 1c. In addition, tension of the second spring 20 holds down the cover 1a via the carrier 16.

Further downward movement of the cover opening mechanism 4 causes the shaft 1 to be biased downward by tension of the first spring 19, thus the cover retainer 17 to be inserted further deeply into the concave portion 1b of the cover 1a, and the annular convex portion 1d of the cover 1a and the annular groove 17a of the cover retainer 17 to become engaged to make the cover retainer 17 retain the cover 1a. This state is shown in FIG. 3. During this engagement, the tension of the first spring 19 inserts the cover retainer 17 into the concave portion 1b of the cover 1a. Additionally, the first spring 19 contracts to absorb the excess of the downward travel of the cover opening mechanism 4, that is, the distance through which the cover opening mechanism 4 may move downward after the cover retainer 17 have fitted into the concave portion 1b of the cover 1a.

Under this state, the rotational driving mechanism 5 rotationally drives the carrier 16 via the rotational drive unit 12, thereby rotating the cover 11. The cover 1a fixed to the openings each having a screw-shaped pitch is then released. At this time, the first spring 19 and the second spring 20 contract to accommodate an upward screwed travel of the cover 1a, associated with the rotation of the cover 1a.

Next, the vertical moving mechanism 6 moves the cover opening mechanism 4 upward until the convex portion 16b on the carrier 16 has abutted the discarding stopper 21, and the horizontal moving mechanism 7 moves it above the discarding box 8.

Upon the cover opening mechanism 4 being moved further upward, upward movement of the carrier 16 is suppressed by the discarding stopper 21, and the cover 1a is held down from above by the carrier 16. The base 15 of the cover opening mechanism 4 is also moved further upward, whereby the stopper 11a, that is, the shaft 11 is biased upward via the third spring 18 and as a result, the engagement between the annular convex portion 1d of the cover 1a and the annular groove 17a of the cover retainer 17 is released. This state is shown in FIG. 4. The cover 1a that has thus been released from the cover retainer 17 drops into the discarding box 8. In addition, the reagent container 1 whose cover has been opened and removed is moved to next process site (e.g., a dispensing site).

After this, the above-described process is repeated for each of any other reagent containers 1 requiring the cover opening process.

Beneficial effects of the present embodiment having the above configuration are described below.

In a conventional technique, while a carrier is configured for vertical movement relative to a centering unit, a snap-in element is fixed in relative form with respect to the centering unit, merely adjusting a vertical position of the centering unit may not suffice for accommodating geometrical or dimensional nonuniformity of a concave portion in a cover of a reagent container, and if the nonuniformity is unaccommodable, the cover opening process could lack reliability since improper hold of the cover is likely. In another conventional technique relating to a cover opener configuration in which a carrier and a centering unit with a snap-in element are fixed in relative form, this configuration is susceptible to not only any geometrical or dimensional nonuniformity of a concave portion in a cover of a reagent container, but also that of the entire cover including a tooth-like structure. If the nonuniformity is unaccommodable, therefore, the cover opening process could lack reliability since improper hold of the cover is likely.

In a cover opener configuration according to an embodiment of the present embodiment, however, a second spring 20 and a first spring 19 contract to absorb a distance through which a cover opening mechanism 4 may move downward after protrusions 16c have fitted into grooves 1c of a reagent container cover 1a, and a distance through which the cover opening mechanism 4 may move downward after a cover retainer 17 has been inserted into a concave portion 1b of the cover 1a, that is, an excess of the downward travel of the cover opening mechanism 4. Geometrical or dimensional nonuniformity of the concave portion 1b in the cover 1a of the reagent container 1 is therefore absorbed, which then enables the cover 1a of the reagent container 1 to be reliably retained and hence the cover 1a to be reliably opened and removed.

DESCRIPTION OF REFERENCE NUMBERS

1 Reagent container
1a Cover
2 Reagent transport disk

3 Cover opener
4 Cover opening mechanism
5 Rotational driving mechanism
6 Vertical moving mechanism
7 Horizontal moving mechanism
8 Discarding box
10 Central axis
11 Shaft
12 Rotationally drive unit
13, 14 Bearings
15 Base
16 Carrier
17 Cover retainer
18 Third spring
19 First spring
20 Second spring
21 Discarding stopper
22 Analyzing unit
23 Reagent replenishing unit
24 Reagent information reading mechanism
25 First reagent container transfer mechanism
26 Replenishment reagent container loading means
27A Reagent container elimination means
27B Receptacle for accommodating eliminated reagent containers
28 Reagent container discarding storage section
29 Second reagent container transfer mechanism
29A, 29B Transport guide rails
30 Dispensing-use reagent container storage section (A)
31 Dispensing-use reagent container storage section (B)
32 Reagent container loading port (A)
33 Reagent container loading port (B)
34 Reagent container rotating mechanism

The invention claimed is:

1. A cover opener for opening a cover rotationally removed from and fixed to a reagent container, the opener comprising:
a rotational drive unit driven by rotational driving means to rotate about a rotational axis of the cover;
a carrier, which is essentially cylindrical and has an open end and a closed end, provided at an opposed position with respect to the cover, including a plurality of projections formed at the open end for engagement with a plurality of grooves spaced from each other on an upper outer circumference of the cover, a first protrusion extending inwardly from the inner wall of the carrier, and a second protrusion extending outwardly from the outer wall of the carrier, the carrier being driven to rotate as the rotational drive unit rotates, and move in the direction of the rotational axis with respect to the rotational drive unit;
a shaft extending along the rotational axis through the rotational drive unit and the carrier, that moves in a direction of the rotational axis with respect to the rotational drive unit and the carrier;
a cover retainer provided at the lower end of the shaft, the cover retainer including a third protrusion extending outwardly along the circumferential direction of the cover retainer, and the cover retainer configured to engage with a concave portion provided on an upper portion of the cover and thereby retain the cover, and upon a downward force exerted on by contact and of the first protrusion and the third protrusion, the cover retainer engages the cover;
a first stopper which confines movement of the carrier by contact with the second protrusion;
a second stopper provided at the upper end of the shaft;
a first biasing means, provided between the rotational drive unit and the cover retainer, for biasing the cover retainer in a direction of axial rotation toward the cover and for biasing the rotational drive unit in a direction opposite to that of the axial rotation of the cover retainer, and the first biasing means biases the rotational drive unit and the cover retainer in relative fashion to move away from each other;
a second biasing means, provided between the rotational drive unit and the carrier, for biasing the carrier in a direction of axial rotation toward the cover and for biasing the rotational drive unit in a direction opposite to that of the axial rotation of the carrier, and the second biasing means biases the rotational drive unit and the carrier in relative fashion to move away from each other; and
a third biasing means, provided on an upper portion of the rotational drive unit, for cushioning the shock between the second stopper and the rotational drive unit.

2. The cover opener according to claim 1, wherein at least one of the first biasing means, the second biasing means, and the third biasing means is a spring.

3. The cover opener according to claim 1, wherein the cover retainer includes a groove provided annularly for engagement with an annular convex portion provided annularly on an inner circumference of the concave portion in the cover.

4. An automatic analyzing device comprising:
an analyzing unit comprising:
a dispensing-use reagent storage section for holding two or more reagent containers holding a reagent, which open and close an opening of a reagent container with a cover, the analyzing unit analyzes using the reagents held in the dispensing-use reagent storage section;
a reagent replenishing unit for holding the reagent containers for replenishing the dispensing-use reagent storage section;
an analyzing mechanism including measuring instruments measuring a sample; and
a reagent container transfer mechanism for transporting the reagent containers between the reagent replenishing unit and the analyzing unit,
wherein the reagent replenishing unit further comprises a cover opener, the cover opener comprising:
a rotational drive unit driven by rotational driving means to rotate about a rotational axis of the cover;
a carrier, which is essentially cylindrical and has an open end and a closed end, provided at an opposed position with respect to the cover, including a plurality of projections formed at the open end for engagement with a plurality of grooves spaced from each other on an upper outer circumference of the cover, a first protrusion extending inwardly from the inner wall of the carrier, and a second protrusion extending outwardly from the outer wall of the carrier, the carrier being driven to rotate as the rotational drive unit rotates, and move in the direction of the rotational axis with respect to the rotational drive unit;
a shaft extending along the rotational axis through the rotational drive unit and the carrier, that moves in a direction of the rotational axis with respect to the rotational drive unit and the carrier;
a cover retainer provided at the lower end of the shaft, the cover retainer including a third protrusion extending outwardly along the circumferential direction of the cover retainer, and the cover retainer configured to engage with a concave portion provided on an upper portion of the cover and thereby retain the cover, and upon a downward force exerted on the third protrusion by contact of the first protrusion and the third protrusion, the cover retainer engages the cover;

a first stopper which confines movement of the carrier by contact with the second protrusion;

a second stopper provided at the upper end of the shaft;

a first biasing means, provided between the rotational drive unit and the cover retainer, for biasing the cover retainer in a direction of axial rotation toward the cover and for biasing the rotational drive unit in a direction opposite to that of the axial rotation of the cover retainer, the first biasing means biases the rotational drive unit and the cover retainer in relative fashion to move away from each other; and a second biasing means, provided between the rotational drive unit and the carrier, for biasing the carrier in a direction of axial rotation toward the cover and for biasing the rotational drive unit in a direction opposite to that of the axial rotation of the carrier, the second biasing means biases the rotational drive unit and the carrier in relative fashion to move away from each other; and a third biasing means, provided on an upper portion of the rotational drive unit, for cushioning the shock between the second stopper and the rotational drive unit, wherein the reagent container opened by the cover opener is transported to the dispensing-use reagent storage section by the reagent container transfer mechanism.

5. The automatic analyzing device according to claim 4, further comprising a discarding mechanism to discard the cover upon removal from the reagent container in the cover opener.

6. An automatic analyzing device according to claim 4, wherein at least one of the first biasing means, second biasing means, and the third biasing means is a spring.

* * * * *